United States Patent
Makin et al.

(10) Patent No.: US 7,303,555 B2
(45) Date of Patent: *Dec. 4, 2007

(54) IMAGING AND THERAPEUTIC PROCEDURE FOR CARPAL TUNNEL SYNDROME

(75) Inventors: Inder Raj S. Makin, Loveland, OH (US); Conrad Lee Klotz, Nappanee, IN (US); Sarah E. Stephens, North Webster, IN (US); Robert J. Dunki-Jacobs, Mason, OH (US)

(73) Assignee: DePuy Products, Inc., Warsaw, IN (US)

( * ) Notice: Subject to any disclaimer, the term of this patent is extended or adjusted under 35 U.S.C. 154(b) by 410 days.

This patent is subject to a terminal disclaimer.

(21) Appl. No.: 10/881,409

(22) Filed: Jun. 30, 2004

(65) Prior Publication Data
US 2005/0038423 A1    Feb. 17, 2005

Related U.S. Application Data

(63) Continuation-in-part of application No. 10/610,463, filed on Jun. 30, 2003, now Pat. No. 7,135,017.

(51) Int. Cl.
*A61B 18/18* (2006.01)
(52) U.S. Cl. .................. 606/28; 600/439; 128/898
(58) Field of Classification Search ............ 606/1, 606/27, 28, 41, 46; 600/439, 471, 1; 128/898
See application file for complete search history.

(56) References Cited

U.S. PATENT DOCUMENTS

| | | | |
|---|---|---|---|
| 4,509,524 A | | 4/1985 | Miwa |
| 4,962,770 A | | 10/1990 | Agee et al. |
| 5,423,804 A | * | 6/1995 | Kulick ................ 606/14 |
| 5,458,130 A | | 10/1995 | Kaufman et al. |
| 5,667,473 A | | 9/1997 | Finn et al. |
| 5,722,411 A | * | 3/1998 | Suzuki et al. .......... 600/439 |
| 5,795,311 A | | 8/1998 | Wess |
| 5,924,999 A | * | 7/1999 | Agee et al. ............. 600/587 |

(Continued)

OTHER PUBLICATIONS

"SafeGuard—Mini Carpal Tunnel Release System", Kinetikos Medical Incorporated (KMI), Apr. 1999 (6 pages).

(Continued)

*Primary Examiner*—Michael Peffley
(74) *Attorney, Agent, or Firm*—Maginot, Moore & Beck (57) ABSTRACT

A system, method and/or apparatus is provided for visualization or imaging of the transverse carpal ligament and surrounding structures/features of a hand of a patient, and treatment of the transverse carpal ligament, particularly, but not necessarily, for performing non-invasive carpal tunnel release. The subject invention utilizes ultrasound waves preferably, but not necessarily, in the high frequency range and cavitations to image the transverse carpal ligament (TCL), record its location in three-dimensional space, and perform precision treatment on the transverse carpal ligament. Treatment may range from stretching or lengthening the TCL to complete tissue ablation or dissection of a portion or portions of the TCL (as is performed in a standard carpal tunnel release procedure) in order to release pressure within the carpal tunnel. Particularly, high temperature conditions are generated at target tissue of the TCL resulting in elongation or necrosis/dissection. The subject system, apparatus and/or method provides the surgeon to relieve a patient of carpal tunnel syndrome symptoms in a bloodless, efficient, and accurate manner.

19 Claims, 10 Drawing Sheets

U.S. PATENT DOCUMENTS

| | | | | |
|---|---|---|---|---|
| 5,954,675 | A | * | 9/1999 | Dellagatta ...................... 601/3 |
| 6,364,849 | B1 | | 4/2002 | Wilcox |
| 7,135,029 | B2 | * | 11/2006 | Makin et al. ............... 606/169 |
| 2004/0019303 | A1 | | 1/2004 | Thomson |
| 2006/0184022 | A1 | * | 8/2006 | Johnson ...................... 600/437 |

OTHER PUBLICATIONS

Viegas, Steven F. et al., "Extra-Bursal Technique of Endoscopic Release of the Carpal Ligament", An Illustrated Guide to the Modified Chow Technique Endoscopic Release of the Carpal Ligament, Smith & Nephew, Inc., Nov. 14, 1997 (12 pages).

"Unparalleled Performance Inside and out", Dec. 2002, Koninklijke Philips Electronics N. V. (16 pages).

"Case Studies—SonoCT® Real-time Compound Imaging", Jun. 2001, Agilent Technologies Healthcare Solutions Group (2 pages).

"Comparison of Image Clarity—SonoCT® Real-time Compound Imaging Versus Conventional 2D Ultrasound Imaging", Agilent Technologies Healthcare Solutions Group, Jun. 2001 (12 pages).

* cited by examiner

IMAGING AND THERAPEUTIC PROCEDURE FOR CARPAL TUNNEL SYNDROME

REFERENCE TO RELATED APPLICATIONS

This application is a continuation-in-part application of U.S. Ser. No. 10/610,463, filed on Jun. 30, 2003 now U.S. Pat. No. 7,135,017 and entitled Imaging and Surgical Procedure for Carpal Tunnel Syndrome. Cross-reference is also made to related U.S. patent application Ser. No. 10/610,474 filed on Jun. 30, 2003 and entitled Surgical Scalpel and System Particularly For Use In a Transverse Carpel Ligament Surgical Procedure.

FIELD OF THE INVENTION

The present invention relates to procedures for relieving problems associated with carpal tunnel syndrome and, more particularly, to a procedure for performing a minimally invasive to non-invasive surgical procedure on a transverse carpal ligament.

BACKGROUND OF THE INVENTION

Carpal tunnel syndrome is a common problem that affects the hand and wrist. This condition, or syndrome, has become the focus of much attention in the last few years due to suggestions that it may be linked to certain occupations that require repetitive use of the hands, such as typing. While certain occupations may experience more problems with carpal tunnel syndrome, many people develop this condition regardless of their occupation.

Particularly, carpal tunnel syndrome (CTS) is a condition that results when the median nerve of the hand does not function properly. Usually, this occurs because there is too much pressure on the median nerve that extends into the wrist through an opening called the carpal tunnel. The median nerve extends into the hand to receive sensation from the thumb, index finger, long finger, and half of the ring finger. The median nerve also provides a branch to the muscles of the thumb (i.e. the thenar muscles).

The carpal tunnel is an opening into the hand that is made up of the bones of the wrist (i.e. the carpals) on the bottom and the transverse carpal ligament on the top. The median nerve and the flexor tendons extend through the carpal tunnel into the hand. The median nerve lies just under the transverse carpal ligament (TCL). A material called the tenosynovium covers the flexor tendons. The tenosynovium is slippery and thus allows the tendons to glide against each other as they move. Any condition that causes irritation or inflammation of the tendons can result in swelling and/or thickening of the tenosynovium. As the tenosynovium begins to swell and/or thicken, pressure begins to increase in the carpal tunnel. This is because the bones and ligaments that form the carpel tunnel are fixed in size and thus are not able to stretch to accommodate the swelling. Increased pressure in the carpel tunnel begins to squeeze the median nerve against the transverse carpal ligament, since the median nerve is the softest structure in the carpal tunnel. Eventually, the pressure reaches a point where the median nerve can no longer function normally. This manifests itself as pain and numbness in the hand.

There are many conditions that can result in irritation and inflammation of the tenosynovium, and eventually cause carpal tunnel syndrome. Different types of arthritis can cause inflammation of the tenosynovium directly. A fracture of the wrist bones may later cause carpal tunnel syndrome if the healed fragments result in abnormal irritation on the flexor tendons. Particularly, anything that causes abnormal pressure on the median nerve will result in the symptoms of carpal tunnel syndrome.

In the early stages of carpal tunnel syndrome, non-operative treatments are typically used. One such non-operative treatment is the use of a brace. The brace keeps the wrist in a neutral position. When the wrist is in a neutral position, the carpal tunnel is as large as it can be so the median nerve has as much room as possible.

Another non-operative treatment that tries to reduce the symptoms of carpal tunnel syndrome is the use of anti-inflammatory medications to help control swelling of the tenosynovium. Anti-inflammatory medications include over the counter medications such as ibuprofen and aspirin, as well as high doses of vitamin B-6. Injections of cortisone into the carpal tunnel may also be used in order to decrease swelling of the tenosynovium and thereby give temporary relief of symptoms.

If the non-operative treatments fail to control the symptoms of carpal tunnel syndrome, surgery may be required to reduce the pressure on the median nerve. There are essentially three surgical techniques designed to relieve pressure on the median nerve. The first and most common surgical procedure is the traditional open incision technique. The second surgical procedure is known as the mini-open. The third procedure is an endoscopic technique.

The traditional open incision technique requires a 2 to 2½ inch incision to be made in the palm of the hand. A structure called the palmer fascia is then incised in order to reach the transverse carpal ligament. The transverse carpal ligament is then cut while making sure that the median nerve is out of the way and protected. The cut or incision may be slight (small incised amount) or drastic (e.g. as in a full carpal tunnel release (CTR) procedure). Pressure on the median nerve is relieved after cutting of the transverse carpal ligament. The incised skin is then sutured. The transverse carpal ligament remains open and the gap is slowly filled by scar tissue.

Major drawbacks to the standard, open incision technique are the slowness of recovery and the size of the resulting scar. Often the 2 inch palm side scar remains sensitive to direct pressure for approximately six to eight weeks. For a working patient, this scar sensitivity may preclude return to normal work activities. Generally, the greater the invasiveness of the remedial methodology, the longer the recovery time is for the patient.

The mini-open technique utilizes a 1 to 1½ cm incision proximate the transverse carpal ligament. Various instruments are placed through the incision and utilized to cut the TCL from underneath as appropriate.

In the endoscopic carpal tunnel release technique, a small horizontal incision is made at the wrist and an arthroscope is introduced underneath the transverse carpal ligament. A small knife or blade, attached to the end of the arthroscope, is utilized to incise or cut the transverse carpal ligament. Again, cutting through the transverse carpal ligament alleviates the compression on the median nerve. While the endoscopic carpal tunnel release technique is less invasive than the traditional, and is typically accomplished on an outpatient basis, it is nonetheless an invasive procedure that requires time to heal. Because the incision is not retracted to provide an open view, a camera probe and light are inserted through small openings placed in the arm or hand to provide the surgeon with a view of the anatomical structure of the surgical site. However, known endoscopic imaging methods may not provide adequate visualization of the TCL and its surrounding structure so some surgeons prefer an open incision technique.

Moreover, with current invasive techniques, the surgeon must rely on his/her own expertise for determining, not only the location and orientation of the initial incision on the palm of the hand, but also in deciding where the transverse carpel ligament should be dissected. The place of dissection is critical because while it is desired to split the transverse carpal ligament, the surgeon must not lacerate any major branch of the median or ulnar nerves.

Although current complication rates are low (approximately 3-4%), inadvertent laceration of a nerve (either fully or partially) can have catastrophic effects on the functionality of the patient's hand. The risk of hand impairment may cause patients suffering from carpal tunnel syndrome to forego surgical remedies of the malady.

In view of the above, a therapeutic technique for performing carpal tunnel release that reduces the risk of median or ulnar nerve laceration is desirable.

Methodologies for encouraging endoscopic procedures are needed to reduce the trauma and recovery time associated with more invasive surgical procedures.

SUMMARY OF THE INVENTION

The subject invention is a system, method and/or apparatus for facilitating minimally invasive to non-invasive surgical treatment of carpal tunnel syndrome. Particularly, the subject invention is a system, method and/or apparatus for performing a minimally invasive to non-invasive transverse carpal ligament treatment procedure.

According to an aspect of the subject invention, three-dimensional imaging of the structures and/or features of a patient's wrist, particularly the internal tissue and/or bone structure(s) of the wrist, is obtained to more accurately identify a target area for dissection of the transverse carpal ligament. The three-dimensional images are stored and evaluated to accurately target therapeutic treatment for and/or on the transverse carpal ligament particularly, but not exclusively, for performing a carpal tunnel release. The three dimensional images are particularly useful for assisting endoscopic surgeons in understanding the images presented by the endoscopic camera located within the patient's hand or wrist so they may safely maneuver instruments within a patient's hand with lower risk of injury or trauma to the internal tissue of the hand.

The imaging methodologies of the present invention also enable a treating physician to more effectively perform non-invasive techniques in accordance with another aspect of the subject invention. The imaging and/or treatment protocols of the present invention may be performed in a non-invasive manner (i.e. without an incision), in a minimally invasive manner (i.e. with a small incision), or even in a fully invasive manner (i.e. with a small to large incision); however, the non-invasive or minimally invasive manners are preferred. The three dimensional imaging methodologies used in the present invention are real time imaging methods, such as spatial compounding ultrasound imaging, computed tomography (CT) imaging, and magnetic resonance imaging (MRI), or the like.

In one form, the three-dimensional imaging locates the transverse carpal ligament particularly with respect to or additionally with the median nerve and/or its branches, carpals, carpal tunnel and/or the like in a patient's hand through the use of ultrasound, preferably, but not necessarily, high frequency ultrasound typically in the 7.5-30 MHz range. The location of the transverse carpal ligament is utilized for commencement of surgical treatment of the transverse carpal ligament ranging from a full carpal tunnel release to a mere cutting or necrosis of a portion of the TCL as well as stretching or relaxing a portion or all of the TCL.

According to another aspect of the subject invention, a surgical procedure on the transverse carpal ligament treats the selected target area or an area near the selected target area. The treatment may include heating the selected target area of the TCL to cause elongation or stretching of the target area(s) of the transverse carpal ligament, or necrosis, ablation and/or dissection of the area(s) of the transverse carpal ligament. The treatment of the selected target area during a surgical procedure may be performed by directly applying ultrasound waves to the target area in the frequency range of about 20 KHz to about 100 KHz.

In one particular form, the subject invention provides a method of performing treatment on a transverse carpal ligament of a wrist of a patient. The method includes the steps of: (a) locating the transverse carpal ligament relative to internal structures proximate the transverse carpal ligament with real time three dimensional images; (b) determining a plan of treatment for a selected target area on the located transverse carpal ligament; and (c) treating the selected target area of the transverse carpal ligament in accordance with the determined plan of treatment.

In another particular form, the subject invention provides a system for performing treatment of the transverse carpal ligament. The system includes: (a) an imager for obtaining a three-dimensional image of a transverse carpal ligament of a wrist of a patient relative to internal structures of the wrist proximate the transverse carpal ligament; (b) a signal generator for generating treatment signals at a selected target tissue area; and (c) an applicator in communication with the generator to apply the generated signals to the selected target tissue area according to the obtained three-dimensional image.

One treatment method performed in accordance with the principles of the present invention includes identifying a target area for an ultrasound treatment and applying ultrasound waves to the target area. The transducer head used to generate and apply the ultrasound waves to the target area may be placed against the patient's skin proximate the TCL or incorporated in a surgical probe having one or more ultrasonic transducers that may be applied to the target area during an endoscopic procedure. The ultrasonic treatment of a patient's TCL may include radiating the TCL with ultrasonic waves in the frequency range of about 20 KHz to about 100 KHz when done during an surgical procedure, including endoscopic procedures, and from about 100 KHz to about 50 MHz for noninvasive therapies. Thus, the frequency range of ultrasound waves used to treat a patient's TCL is wider than the range of imaging ultrasound waves. Additionally, the target area of the TCL may be radiated with more than one frequency of ultrasound waves, either substantially at the same time or sequentially. The duration of the periods of application for the ultrasound treatment waves may be the same or different for the various frequencies used in the treatment. Also, the ultrasound waves may be applied in a variety of field patterns, including, but not limited to, circular spot, ellipsoid spot, and rectangular spot and one or more application patterns may be used during application of a treatment.

The ultrasound treatment methodology of the present invention may also include monitoring the effects of the ultrasound bombardment of the target area. This monitoring may include determining the degree of acoustic speed through the target tissue, the attenuation of acoustic energy by the target tissue, the change in density in the target tissue, the temperature of the target tissue, or the non-linearity of the target tissue's response to the ultrasound waves. These monitored effects may be used to select one or more frequencies for the treatment, application durations for ultrasound waves, or other treatment parameters.

Another method that may be performed in accordance with the principles of the present invention includes administering drug therapy to the target site and applying ultrasound waves to the target site to enhance the effectiveness of the drug therapy. The administered drugs include local anti-inflammatory medicines, local analgesic medications, and steroid-based anti-inflammatory compounds. These ultrasound treatments enhance the shrinking or inflammation reduction effects of these drugs at the target area. Local anti-inflammatory drugs include ibuprofen and the like, local analgesic medicines include aspirin, and steroid-based anti-inflammatory medications include hydrocortisone or the like.

The subject invention provides the benefits of: i) a minimally invasive to non-invasive, bloodless and relatively painless surgical procedure; ii) a greater degree of visualization to assist a surgeon in the maneuvering of instruments within a patient's hand; and iii) a decrease in risk of injury or recovery time to patients.

BRIEF DESCRIPTION OF THE DRAWINGS

In the drawings.

Corresponding reference characters indicate corresponding parts throughout the several views. Like reference characters tend to indicate like parts throughout the several views.

DETAILED DESCRIPTION OF THE INVENTION

While the invention is susceptible to various modifications and alternative forms, specific embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention.

Figure 1:
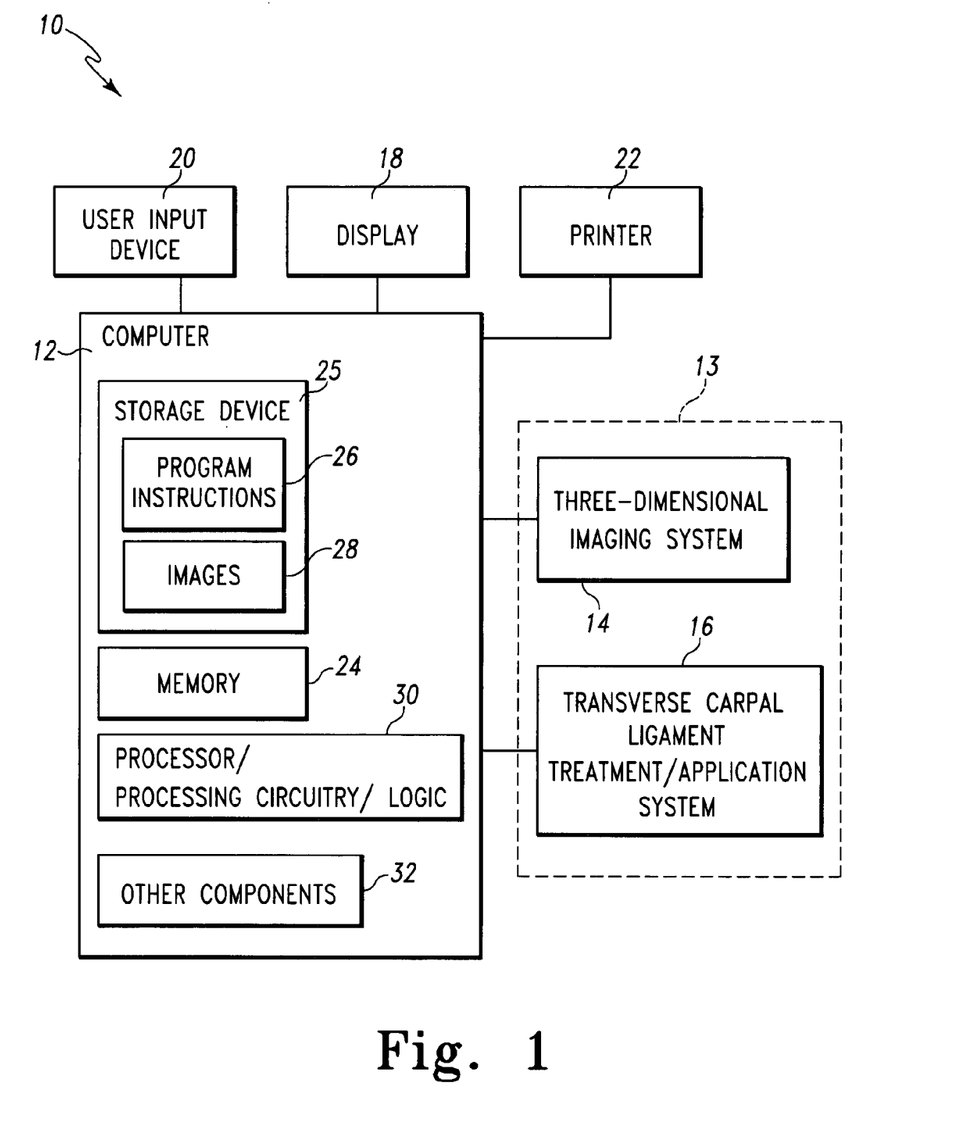
FIG. 1 is a block diagram of a non-invasive treatment system for carpal tunnel problems in accordance with the principles of the subject invention.

Referring now to FIG. 1 there is shown a block diagram of an exemplary system, generally designated 10, for three-dimensional (3-D) imaging of a transverse carpal ligament of a wrist of a hand and providing treatment (preferably, but not necessarily in a non-invasive manner) to the wrist area of a patient, particularly the transverse carpal ligament such as for relieving carpal tunnel syndrome and/or its symptoms. The system 10 provides for the three-dimensional imaging and the recording of the location of at least the transverse carpal ligament and preferably, the transverse carpal ligament and surrounding structures or features of a patient's wrist. The system 10 also provides for treatment to the transverse carpal ligament that is preferably, but not necessarily, based on the 3-D imaging thereof. The treatment ranges from stretching or elongation of a target area or target areas of the transverse carpal ligament to complete tissue ablation, necrosis and/or dissection of the transverse carpel ligament at the target area.

The system 10 produces a therapeutic condition, such as an elevated temperature condition, at a target area of a particular tissue or tissue type. This may be accomplished in a non-invasive manner or in a minimally invasive manner. It should be appreciated that while the subject invention is applicable for use in both non-invasive and minimally invasive manners, the subject invention is preferably used in a non-invasive manner. Therefore while hereinafter the term non-invasive is used with respect to the subject invention, invasive manners are covered as well. The therapeutic condition is produced by energy waves particularly pressure waves, such as ultrasound. The pressure wave may be shaped as appropriate for the target area.

The system 10 may be used for performing a non-invasive carpal tunnel release procedure on the target area(s) of the transverse carpal ligament, typically for alleviating problems and/or symptoms associated with carpal tunnel syndrome, or a lesser procedure on the transverse carpal ligament. In this manner, the pressure within the carpal tunnel or canal is relieved in a bloodless, efficient and accurate manner. It should be appreciated that while the system will be described with respect to the transverse carpal ligament and/or wrist area, particularly for carpal tunnel release, the subject invention may be used for other tissue types and/or tissue areas.

The system 10 includes a computer, processing device, or other similar device 12 such as is known in the art. The computer 12 has a storage device 25, such as a hard drive, that stores program instructions 26 for the operation of the computer and for the operation, features and/or functionality of the subject invention as well as the functionality of the various components of the computer 12 and the various components of the system 10 as herein provided. As discussed below, the storage device 25 also stores still images and video (images) 28 as acquired and includes 3-D modeling and imaging software, treatment software, diagnostic software, interface software, and the like. The storage device 25 is operative to store, receive and allow deletion therefrom of various types of data. Memory 24 is also provided such as RAM for temporarily storing data and program instructions for execution and/or ROM for permanently storing data such as is known in the art.

A user input device such as a keyboard and/or mouse 20 is operatively connected to the computer 12. The user input device 20 is operative to accept or receive input from a user for operation of the subject invention. A display 18 is also coupled or connected to the computer 12 and is adapted to display images/video (including program interfaces, e.g. GUIs) thereon as received from the computer 12. Optionally, a printer 22 is operatively coupled or connected to the computer 12. If provided, the printer 22 is preferably a high resolution printer. The printer 22 is adapted to receive and print images, text and/or the like as necessary.

The computer 12 also includes a processor and/or processing circuitry/logic 30 that is operative, adapted and/or configured to utilize the program instructions 26 and/or control the various components of the computer 12 and/or the system 10. Other components of the computer 12 not described herein but which are typically part of a computer such as communication hardware, display adaptors, and/or the like are represented by the other components box 32.

In accordance with an aspect of the subject invention, the system includes an imaging and treatment portion, section, sub-system, or the like, generally designated 13. The imaging and treatment portion 13 may be separate from the computer 12 or may be at least partially integral with the computer 12 as represented by the dashed lines. In either case, the functioning is the same. The imaging and treatment portion 13 is configured, adapted and/or operative to perform three-dimensional tissue imaging, both static and dynamic, such as a transverse carpal ligament and surrounding structures/features, and provide treatment to a target area of the imaged tissue. The imaging and treatment portion also obtains data that is formed into the three-dimensional image. The obtained image is preferably stored in the images section 28 of the storage device 25.

Particularly, the imaging and treatment portion 13 includes a three-dimensional imaging system 14 and a tissue (transverse carpal ligament) treatment system 16. The imaging portion 14 obtains tissue images while the treatment/application portion 16 provides a non-invasive procedure that induces, generates, creates or produces an elevated temperature condition at the target tissue area preferably, but not necessarily, in accordance with the imaging, and at least with respect to a determined plan of treatment typically selected with regard to the imaging. The elevated temperature condition is localized heating of the target tissue area to a point where the target tissue is stretched or elongated, tissue ablation occurs at the target tissue area, tissue necrosis, tissue dissection, or other appropriate treatment effect on the tissue. The system 13 can provide intervals of imaging and treatment until a desired outcome is produced.

Figure 2:
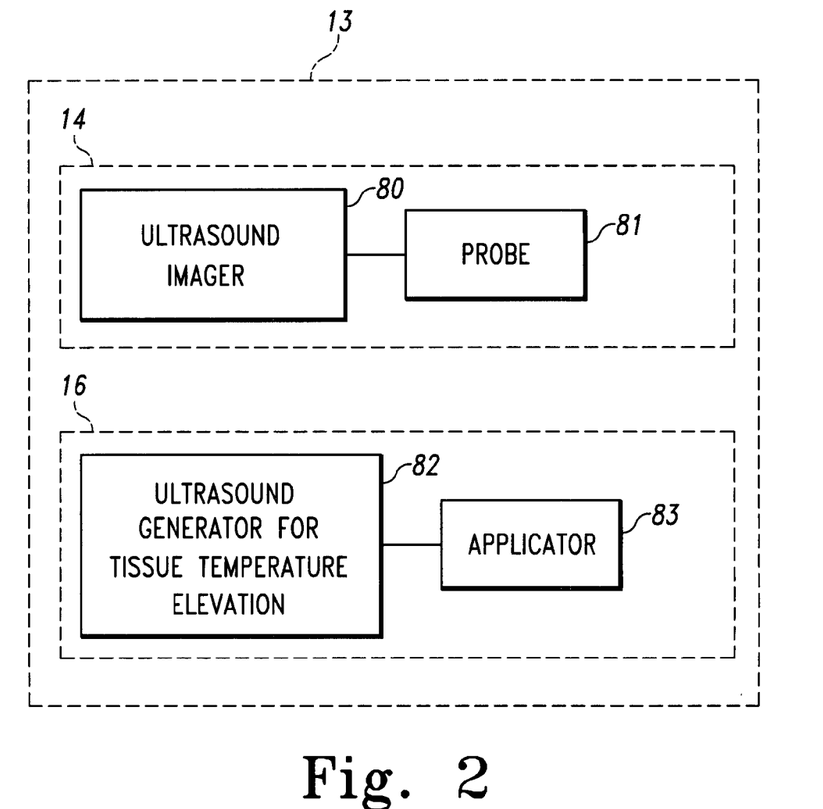
FIG. 2 is a block diagram of an exemplary embodiment of an imaging and treatment portion of the non-invasive treatment system of FIG. 1.

In FIG. 2 there is depicted a block diagram of an exemplary embodiment of the imaging and treatment portion 13 of the non-invasive diagnostic and treatment system 10 of FIG. 1. The imaging portion 14 is shown as including an ultrasound imager 80 and a probe 81 connected thereto. The treatment portion 16 is shown as including an ultrasound generator 82 and an applicator 83 connected thereto. It should be appreciated, however, that other imaging systems or imagers may be used such as MRIs, CAT scans, and/or the like.

The imaging portion 14 is operatively coupled or connected to the computer 12. The ultrasound imager 80 is configured, adapted and/or operative to cause the production or generation of ultrasound waves at a particular ultrasound frequency or at one or more of a plurality of ultrasound frequencies. The ultrasound imager 80 preferably is operative to controllably cause the production or generation of ultrasound in a frequency range of about 1.0 MHz to 35 MHz. Typically, low frequency ultrasound in the 1.0 to 7.5 MHz range is used for diagnostics/imaging and ultrasound in the frequency range of about 20 KHz to about 50 MHz may be used for treatment as described herein.

An ultrasound probe 81 is operatively coupled or connected to the ultrasound imager 80. The probe 81 is adapted, configured and/or operative to produce, generate and/or emit the ultrasound waves in accordance with the ultrasound imager 80. The probe 81 thus serves as a source for ultrasound waves or signals used for imaging. The probe 81 is also adapted, configured and/or operative to receive the ultrasound signals/waves that are reflected from or echo off of the internal wrist structures (tissues) and convert the received reflected ultrasound signals/waves into electrical signals. The received ultrasound signals/waves, being converted into electrical signals, are received by the ultrasound imager 80 to produce a reflected pattern. The reflected pattern is utilized by appropriate program instructions 26 to produce an image.

The probe 81 may be moved to provide three-dimensional imaging of the internal wrist structures including the transverse carpal ligament and location with respect to the other internal wrist structures. The probe 81 may be designed to be situated about the wrist such that various angles of ultrasound signals are produced and reflections received that provide a three-dimensional image of the wrist structures, particularly the transverse carpal ligament, carpal tunnel, and other adjacent structures. These images may be displayed for educating a treating physician regarding the structure of an area to be treated, for assisting a treating physician in visualizing what the physician is viewing during an endoscopic procedure, and/or for enabling a treating physician to select a target area for therapeutic treatment.

While the ultrasound imager 80 is shown as a separate component, it should be appreciated that part or all of the ultrasound imager and/or its functionality may be incorporated into or as part of the computer 12 and/or its various components. In this case, the probe 81 may be directly coupled to the computer 12.

The treatment portion 16 is operatively coupled or connected to the computer 12. The treatment portion 16 is configured, adapted and/or operative to cause the production or generation of ultrasound waves or signals capable of providing therapeutic treatment of internal tissue at a target area. The treatment portion 16 includes an ultrasound generator 82 capable of providing ultrasound waves for therapeutic treatment of the tissue target area. An applicator 83 is operatively coupled or connected to the ultrasound generator 82. The applicator 83 is adapted, configured and/or operative to produce, generate and/or emit the ultrasound waves in accordance with the ultrasound generator 82. The applicator 83 thus serves as a source for the treatment ultrasound waves or signals.

The applicator 83 may be moved to provide treatment to a specific target area or target areas (collectively, target area) of the particular tissue undergoing treatment. The applicator 83 may be designed to be situated about the wrist such that various angles of ultrasound treatment signals are produced, particularly for treatment of the transverse carpal ligament.

While the ultrasound generator 82 is shown as a separate component, it should be appreciated that part or all of the ultrasound generator and/or its functionality may be incorporated into or as part of the computer 12 and/or its various components. In this case, the applicator 83 may be directly coupled to the computer 12.

Figure 3:
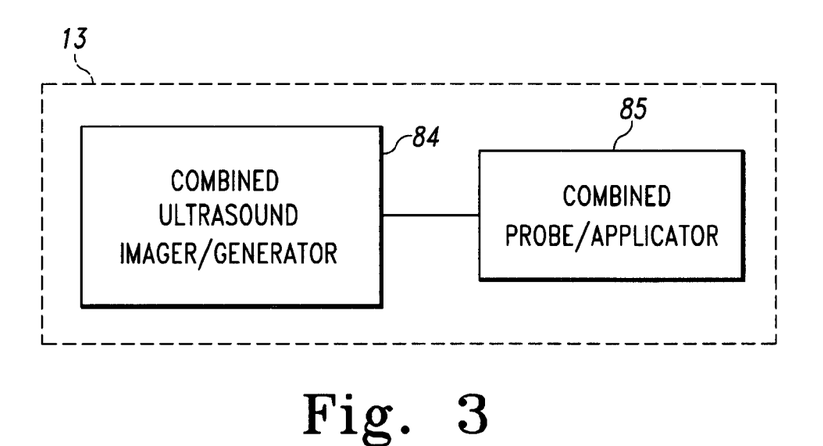
FIG. 3 is a block diagram of another exemplary embodiment of an imaging and treatment portion of the non-invasive treatment system of FIG. 1.

Referring to FIG. 3, there is depicted a block diagram of another exemplary embodiment of the imaging and treatment portion 13. In this embodiment, a combined ultrasound imager and generator 84 substitute for the separate ultrasound imager 14 and the ultrasound generator 82 of FIG. 2. The combined ultrasound imager/generator 84 is configured, operative and/or adapted to perform in the same manner as described above for the separate components. Moreover, the imaging and treatment portion 13 includes a combined probe/applicator 85 that likewise, combines the functionality of the probe 81 and applicator 83 of FIG. 2 into a single unit.

It should be appreciated that while the ultrasound imager/generator 84 is shown as a separate component, part or all of the ultrasound imager/generator and/or its functionality may be incorporated into or as part of the computer 12 and/or its various components. In this case, the probe/applicator 85 may be directly coupled to the computer 12.

Figure 4:
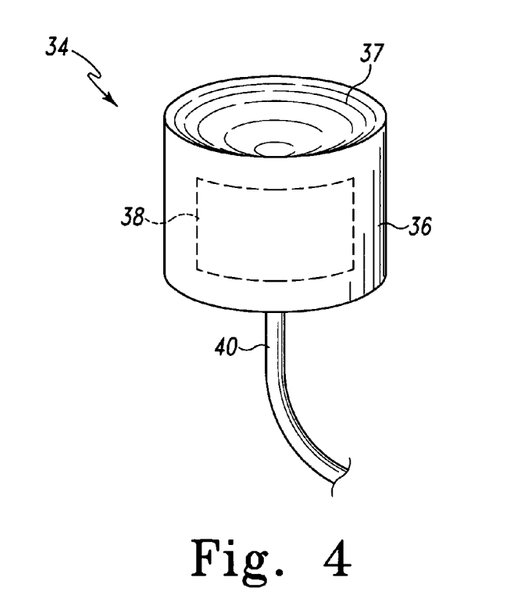
FIG. 4 is a perspective view of an exemplary configuration of a combined probe/applicator for imaging a transverse carpal ligament and surrounding structures of the wrist and/or treatment thereof in accordance with the present principles.

Referring now to FIG. 4, there is depicted an exemplary embodiment of a probe and/or treatment/applicator device generally designated 34. The probe/treatment (or probe/applicator) device 34 is an exemplary embodiment of one of the probe 81, the applicator 83, or the combined probe/applicator 85 (collectively hereinafter, probe/applicator device). The probe/applicator device 34 is operative, adapted and/or configured to produce and emit ultrasound waves and receive reflected ultrasound waves. The probe/applicator device 34 has a body or shell 36 that is formed as an essentially large diameter, small (axial) length cylinder having an essentially round head 37. The head 37 is utilized to abut or be in contact with the skin, typically via a transmission jelly such as in known in the art. As such, the head 37 is shaped accordingly to take into account the typical shape of a wrist.

The body 36 houses a transducer 38 such as a piezoelectric crystal. The transducer 38 is operative to produce and emit ultrasound waves of the appropriate frequency and receive (capture) reflected ultrasound waves. The transducer 38 converts the captured ultrasound waves into electrical signals that are transmitted via conductor 40 to the ultrasound imaging device/generator 14 and/or the computer 12.

While depicted as a single device, the transducer 38 may be two separate devices. One device would be the ultrasound source, while the other device would be the ultrasound receiver. The source device may constitute a single transducer or an array of transducers for three-dimensional imaging. The receiver device likewise may be a single transducer of an array of transducers. Moreover, the housing 36 is sized to be positioned over and/or around the wrist of a patient.

Figure 5:
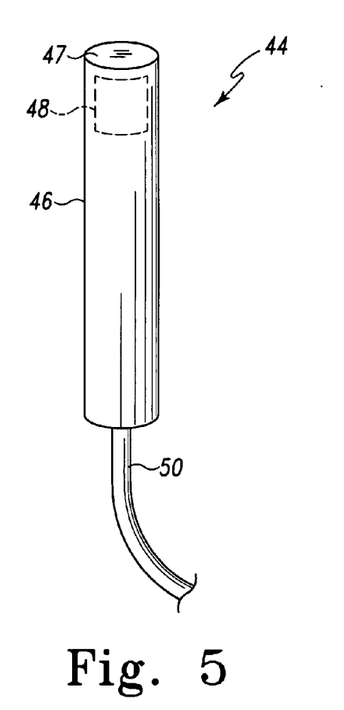
FIG. 5 is a perspective view of another exemplary configuration of a combined probe/applicator for imaging a transverse carpal ligament and surrounding structures of the wrist and/or treatment thereof in accordance with the present principles.

Referring now to FIG. 5, there is depicted another exemplary embodiment of a probe and/or treatment/applicator device generally designated 44. The probe/treatment (or probe/applicator) device 44 is an exemplary embodiment of one of the probe 81, the applicator 83, or the combined probe/applicator 85 (collectively hereinafter, probe/applicator device). The probe/applicator device 44 is operative, adapted and/or configured to produce and emit ultrasound waves and receive reflected ultrasound waves. The probe/applicator device 44 has a body or shell 46 that is formed as an essentially small diameter, large (axial) length cylinder having an essentially round head 47. The head 47 is utilized to abut or be in contact with the skin, typically via a transmission jelly such as in known in the art. As such, the head 47 is shaped accordingly to take into account the typical shape of a wrist.

The body 46 houses a transducer 48 such as a piezoelectric crystal. The transducer 48 is operative to produce and emit ultrasound waves of the appropriate frequency and receive (capture) reflected ultrasound waves. The transducer 48 converts the captured ultrasound waves into electrical signals that are transmitted via conductor 50 to the ultrasound imaging device/generator 14 and/or the computer 12.

While depicted as a single device, the transducer 48 may be two separate devices. One device would be the ultrasound source, while the other device would be the ultrasound receiver. The source device may constitute a single transducer or an array of transducers for three-dimensional imaging. The receiver device likewise may be a single transducer of an array of transducers. Moreover, the housing 46 is sized to be positioned over and/or around the wrist of a patient.

Figure 6:
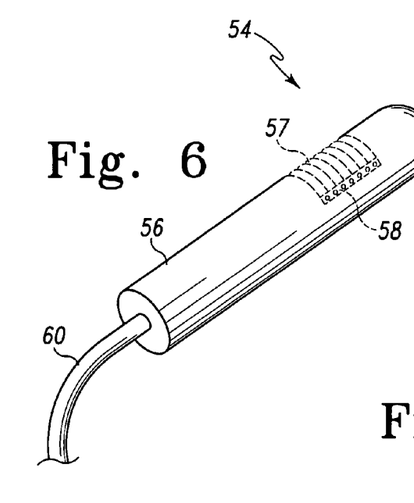
FIG. 6 is a perspective view of yet another exemplary configuration of a combined probe/applicator for imaging a transverse carpal ligament and surrounding structures of the wrist and/or treatment thereof in accordance with the present principles.

Referring now to FIG. 6, there is depicted yet another exemplary embodiment of a probe and/or treatment/applicator device generally designated 54. The probe/treatment (or probe/applicator) device 54 is an exemplary embodiment of one of the probe 81, the applicator 83, or the combined probe/applicator 85 (collectively hereinafter, probe/applicator device). The probe/applicator device 54 is operative, adapted and/or configured to produce and emit ultrasound waves and receive reflected ultrasound waves. The probe/applicator device 54 has a body or shell 56 that is formed as an elongated wand. The wand 56 has a transmission/reception area 57 that is shaped to contact the wrist area of the hand of the patient.

The body 56 houses a transducer 58 such as a piezoelectric crystal. The transducer 58 is operative to produce and emit ultrasound waves of the appropriate frequency and receive (capture) reflected ultrasound waves. The transducer 58 converts the captured ultrasound waves into electrical signals that are transmitted via conductor 50 to the ultrasound imaging device/generator 14 and/or the computer 12.

While depicted as a single device, the transducer 58 may be two separate devices. One device would be the ultrasound source, while the other device would be the ultrasound receiver. The source device may constitute a single transducer or an array of transducers for three-dimensional imaging. The receiver device likewise may be a single transducer of an array of transducers.

Figure 7:
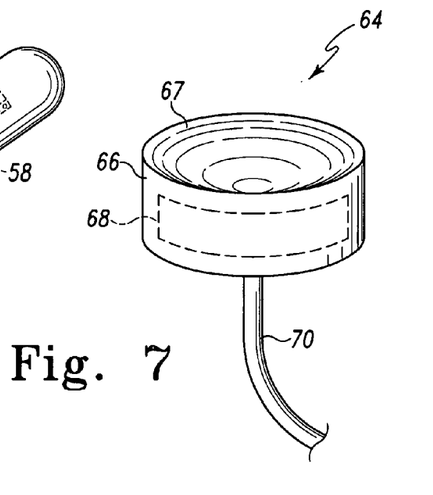
FIG. 7 is a perspective view of still another exemplary configuration of a combined probe/applicator for imaging a transverse carpal ligament and surrounding structures of the wrist and/or treatment thereof in accordance with the present principles.

Referring now to FIG. 7, there is depicted another exemplary embodiment of a probe and/or treatment/applicator device generally designated 64. The probe/treatment (or probe/applicator) device 64 is an exemplary embodiment of one of the probe 81, the applicator 83, or the combined probe/applicator 85 (collectively hereinafter, probe/applicator device). The probe/applicator device 64 is operative, adapted and/or configured to produce and emit ultrasound waves and receive reflected ultrasound waves. The probe/applicator device 64 has a body or shell 66 that is formed as an essentially large diameter, small (axial) length cylinder having an essentially oval and/or curved head 67. The head 67 is utilized to abut or be in contact with the skin and be around at least 180° around the wrist, typically via a transmission jelly such as in known in the art. As such, the head 67 is shaped accordingly to take into account the typical shape of a wrist.

The body 66 houses a transducer 68 such as a piezoelectric crystal. The transducer 68 is operative to produce and emit ultrasound waves of the appropriate frequency and receive (capture) reflected ultrasound waves. The transducer 68 converts the captured ultrasound waves into electrical signals that are transmitted via conductor 60 to the ultrasound imaging device/generator 14 and/or the computer 12.

While depicted as a single device, the transducer 68 may be two separate devices. One device would be the ultrasound source, while the other device would be the ultrasound receiver. The source device may constitute a single transducer or an array of transducers for three-dimensional imaging. The receiver device likewise may be a single transducer of an array of transducers. Moreover, the housing 66 is sized to be positioned over and/or around the wrist of a patient.

Figure 8:
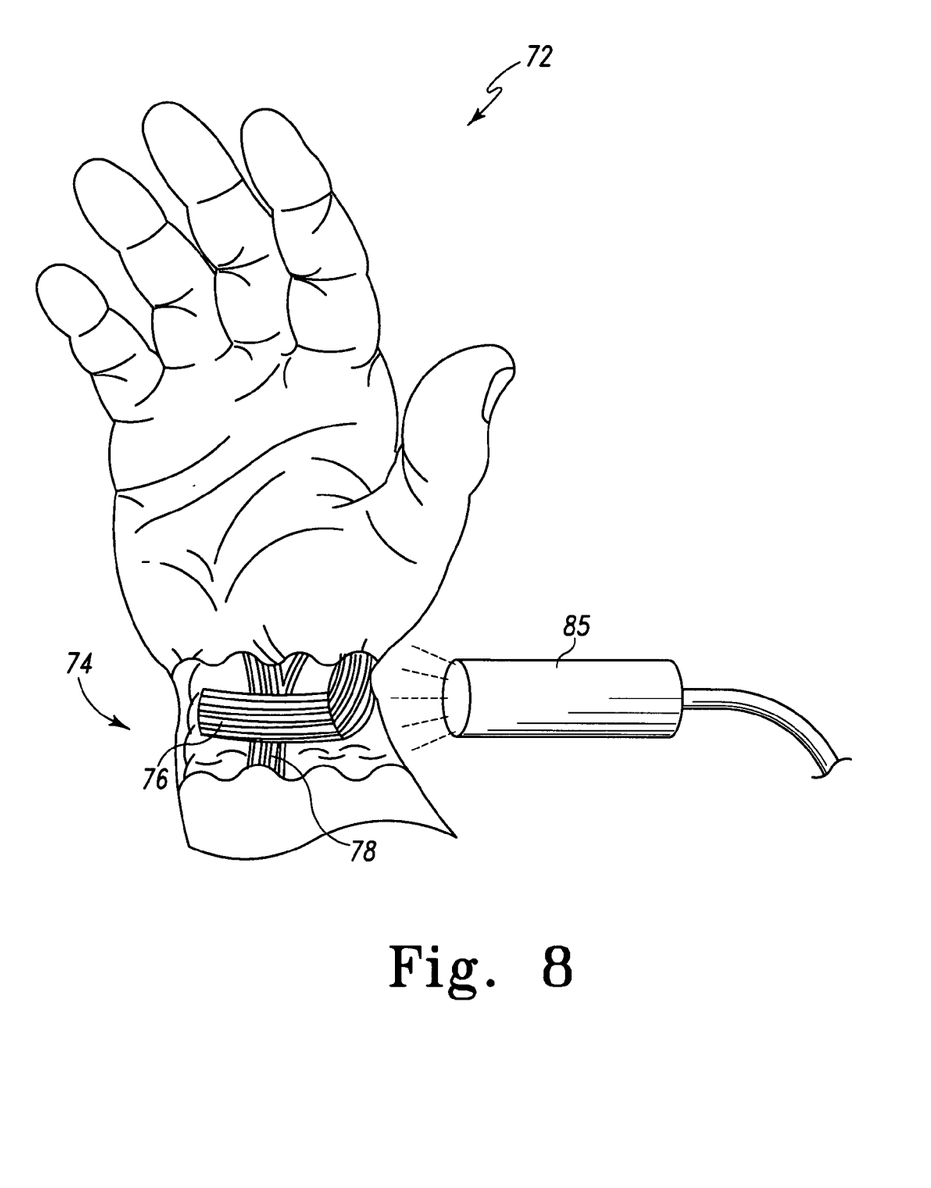
FIG. 8 is an illustration of an imaged wrist of a hand of a patient receiving treatment in accordance with the present principles.

In FIG. 8, there is depicted a hand 72 of a patient in order to illustrate an exemplary manner of utilizing the system 10 and of an exemplary manner of performing a non-intrusive carpal tunnel release. The wrist area 74 of the hand 72 has been imaged in 3-D, particularly the transverse carpal ligament 76, by a combined probe/applicator 85. The transverse carpal ligament 76 is shown in relation to the median nerve 78. The 3-D imaging is preferably stored and used in determining an appropriate treatment for the transverse carpal ligament 76. The transverse carpal ligament 76 is also located with respect to other features or structures of the wrist 74 that are not shown.

The probe/applicator 84 is providing preferably high-frequency ultrasound treatment to a selected or particular target area or areas of the transverse carpal ligament. Depending on the frequency and/or length of time of exposure, the target area tissue will be elongated (stretched), ablated, dissected, or be subject to necrosis. Of course, other probe shapes may be utilized.

Figure 9:
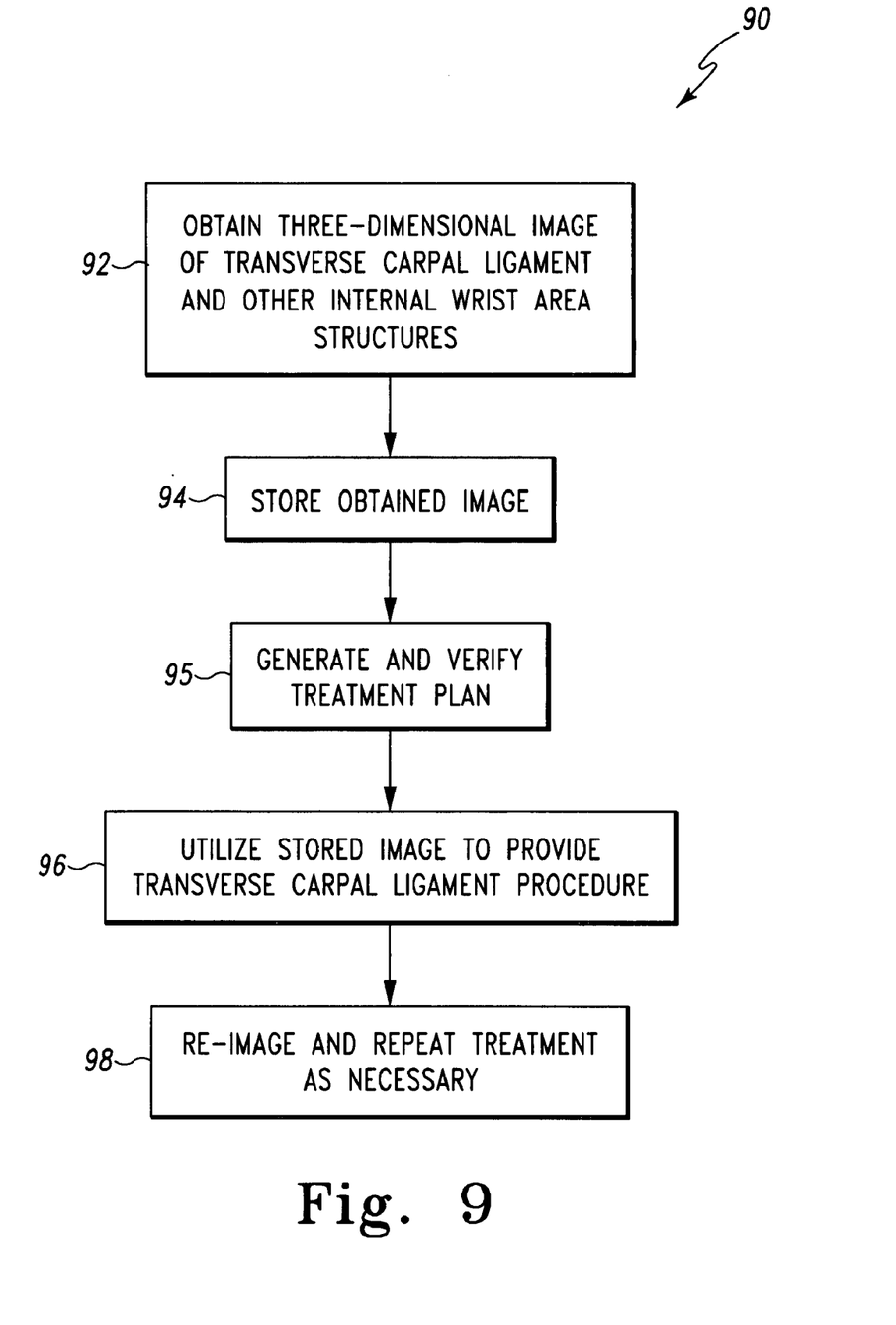
FIG. 9 is a flowchart of an exemplary carpal tunnel release procedure in accordance with the present principles.

Referring now to FIG. 9, there is depicted a flowchart, generally designated 90, of an exemplary manner of performing a non-intrusive carpal ligament release in accordance with the present principles and preferably, but not necessarily, using the present system 10. In step or block 92, a three-dimensional image of a transverse carpal ligament and other internal wrist structures is obtained. In step 94, the obtained three-dimensional image is stored. In step 96, the stored three-dimensional image is utilized to provide a non-invasive carpal tunnel release (CTR) procedure. The procedure of step 96 may entail a complete treatment, or may entail a partial treatment. For a partial treatment, after a first treatment, the transverse carpal ligament may be re-imaged and treatment is repeated. The repeated treatment may be to the same target area or to a different target area.

Figure 9A:
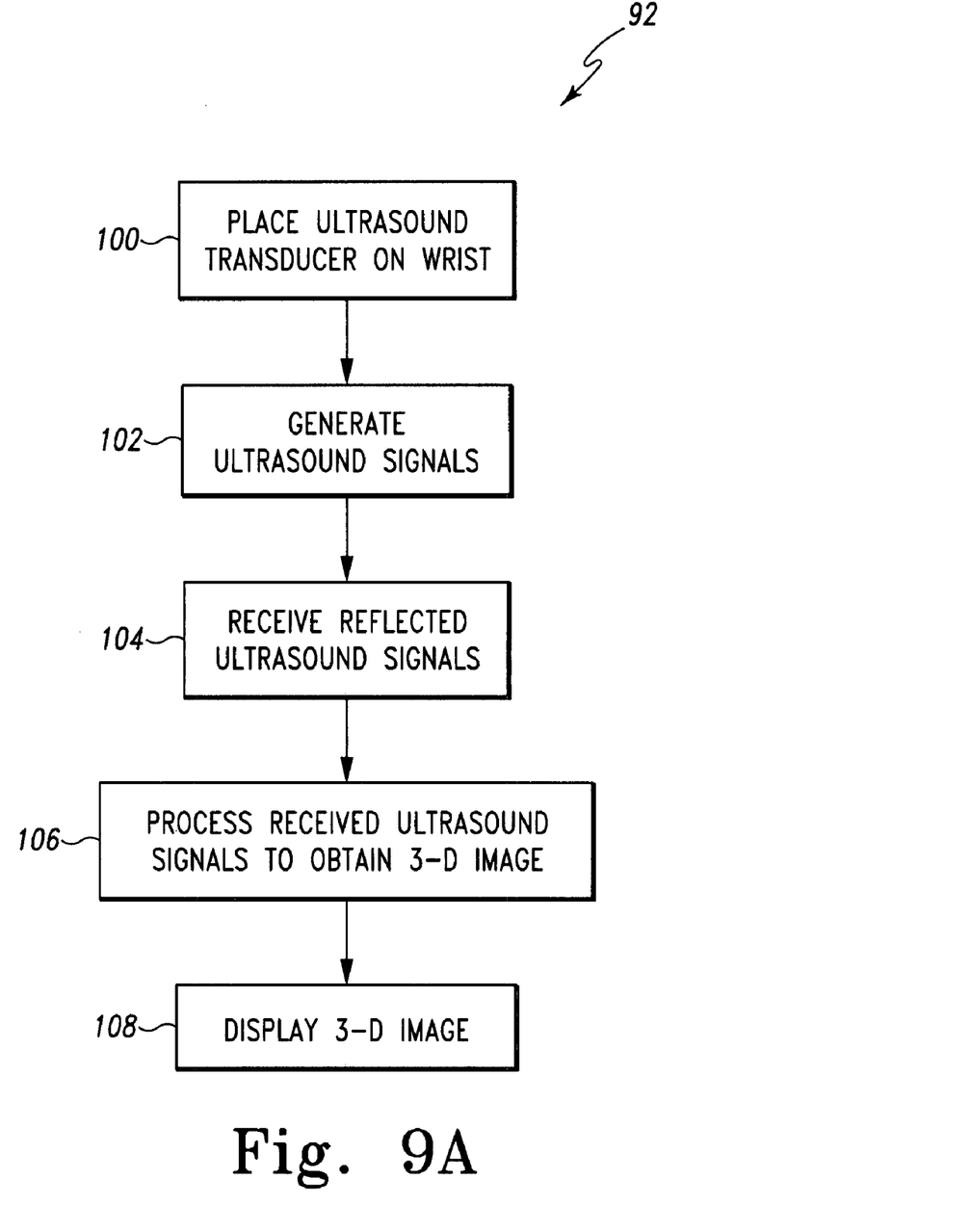
FIG. 9A is a flowchart of an exemplary manner of carrying out a step of the flowchart of FIG. 9.

In FIG. 9A, an expanded flowchart of step 92 is shown. It should be appreciated that the expanded flowchart of step 92 is only exemplary of a manner of executing step 92. In step 100, an ultrasound transducer is placed on the wrist of a patient. In step 102, ultrasound signals are generated that are transmitted into the wrist area. In step 104, ultrasound signals that are reflected by the underlying tissue/tissue structures (including the transverse carpal ligament and the median nerve) are received by the probe. The signals, in step 106, are processed to obtain a three-dimensional image of the transverse carpal ligament and its relationship to the other structures of the wrist. Optionally, in step 108, the generated three-dimensional image is displayed.

Figure 9B:
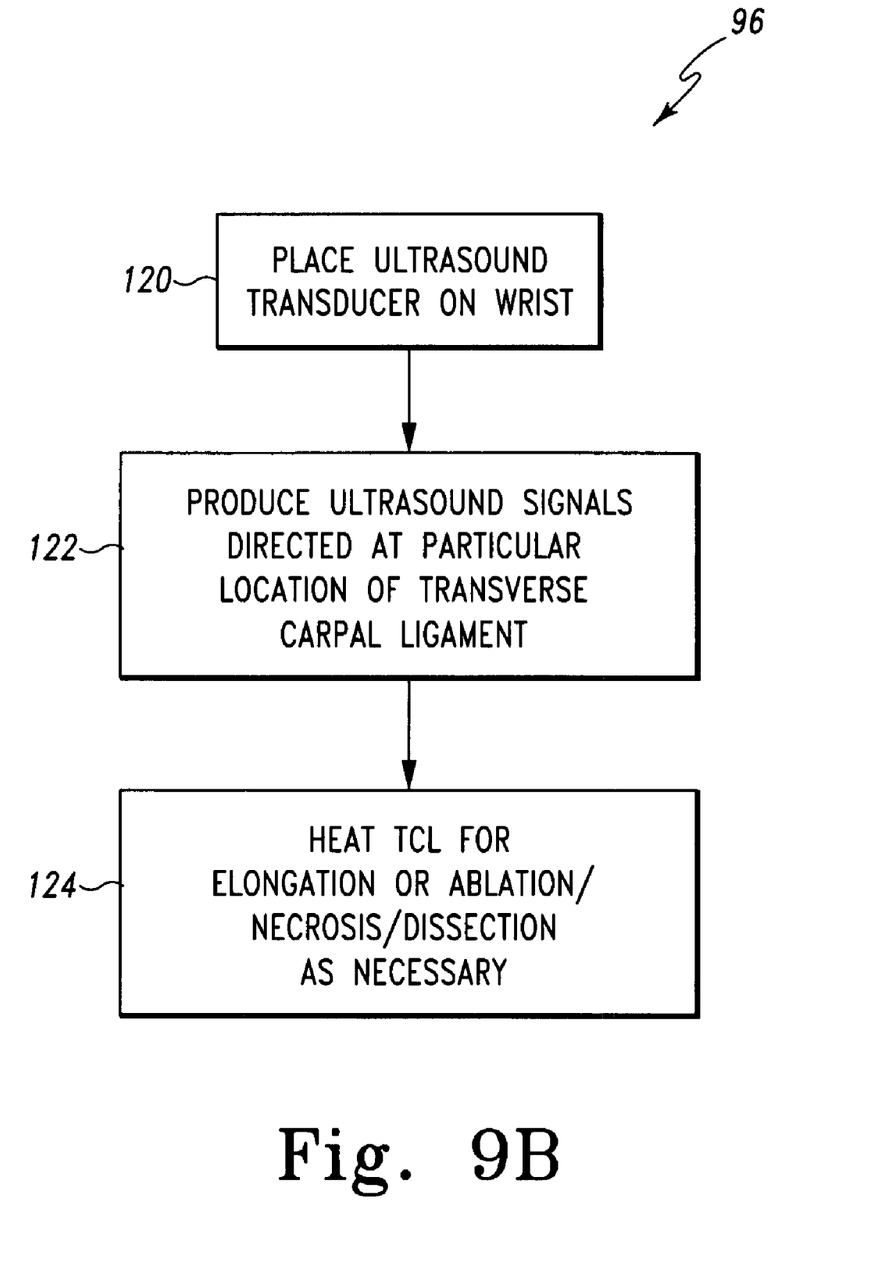
FIG. 9B is a flowchart of an exemplary manner of carrying out another step of the flowchart of FIG. 9.

In FIG. 9B, an expanded flowchart of step 96 is shown. It should be appreciated that the expanded flowchart of step 96 is only exemplary of a manner of executing step 96. In step 120, an ultrasound transducer (applicator) is strategically placed on the wrist to be imaged. In step 122, high frequency ultrasound signals are generated and directed at a particular location (target area) of the transverse carpal ligament. In step 124, the target location of the transverse carpal ligament is heated by the ultrasound signals to provide elongation, ablation, necrosis and/or dissection as appropriate.

Figure 10:
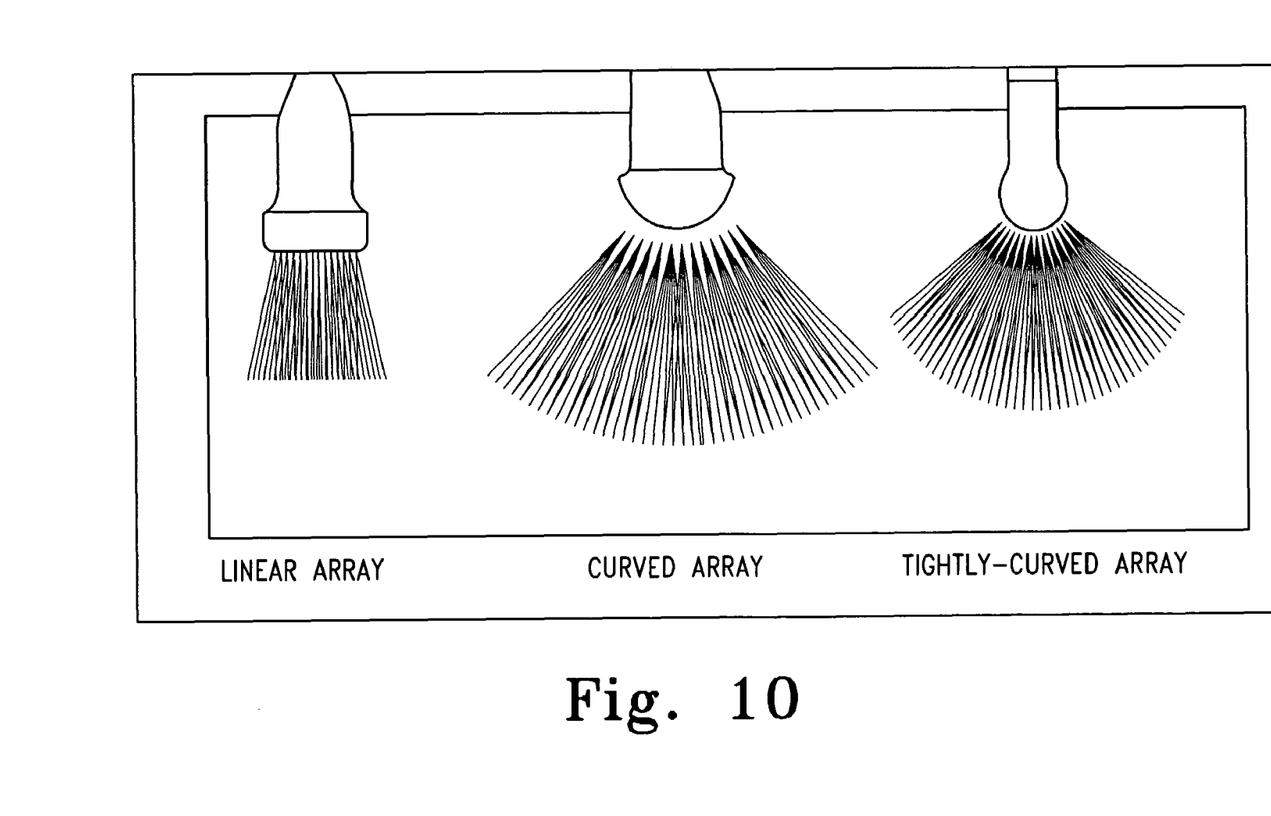
FIG. 10 is an illustration of various transducer arrangements that may be used to implement the principles of the present invention.

The principles of the present invention may be implemented with an HDI 5000 ultrasound imaging system that is available from Philips Medical Systems Company, of Bothell, Wash. Such a system uses different lines of sight for the radiation used to image an area to provide three dimensional images. A representative method of generating ultrasound images is sometimes called spatial compounding. This type of imaging may be achieved with various shapes of ultrasound probes, such as the ones shown in FIG. 10. The transducer arrays in these probes may be described as linear, curved, or tightly curved arrays. The transducers that may be used in this type of imaging include broadband curved, linear and phased array transducers. The imaging system 14 of the present invention may also be implemented with computed tomography (CT) images that may be obtained from known CT scanners.

The three dimensional images obtained of the carpal tunnel area enable a treating physician to more accurately identify a target area for treatment. As described above, these images may be stored and displayed for various purposes. For one, they may be used to educate a treating physician regarding the form and location of soft tissue structure. For another, they may be displayed during the performance of an endoscopic procedure to aid a surgeon in the understanding the images provided by an endoscopic camera. The images may also be displayed so a surgeon or other treating physician may select a target area that is sufficiently removed from the median or ulnar nerve that the risk of severing the nerve is substantially reduced.

An ultrasound imaging system may be modified to provide a tissue treatment system 16 that generates ultrasound signals in the range of approximately 1 MHz to approximately 35 MHz. Depending on the type of transducer probe used, the acoustic energy from the probe may be focused on a small target area or spread over a broader target area. For example, the linear and curved transducer arrays of FIG. 10 cover wider areas than the more focused field that emanates from the tightly curved transducers of the tightly curved probe.

Figure 11:
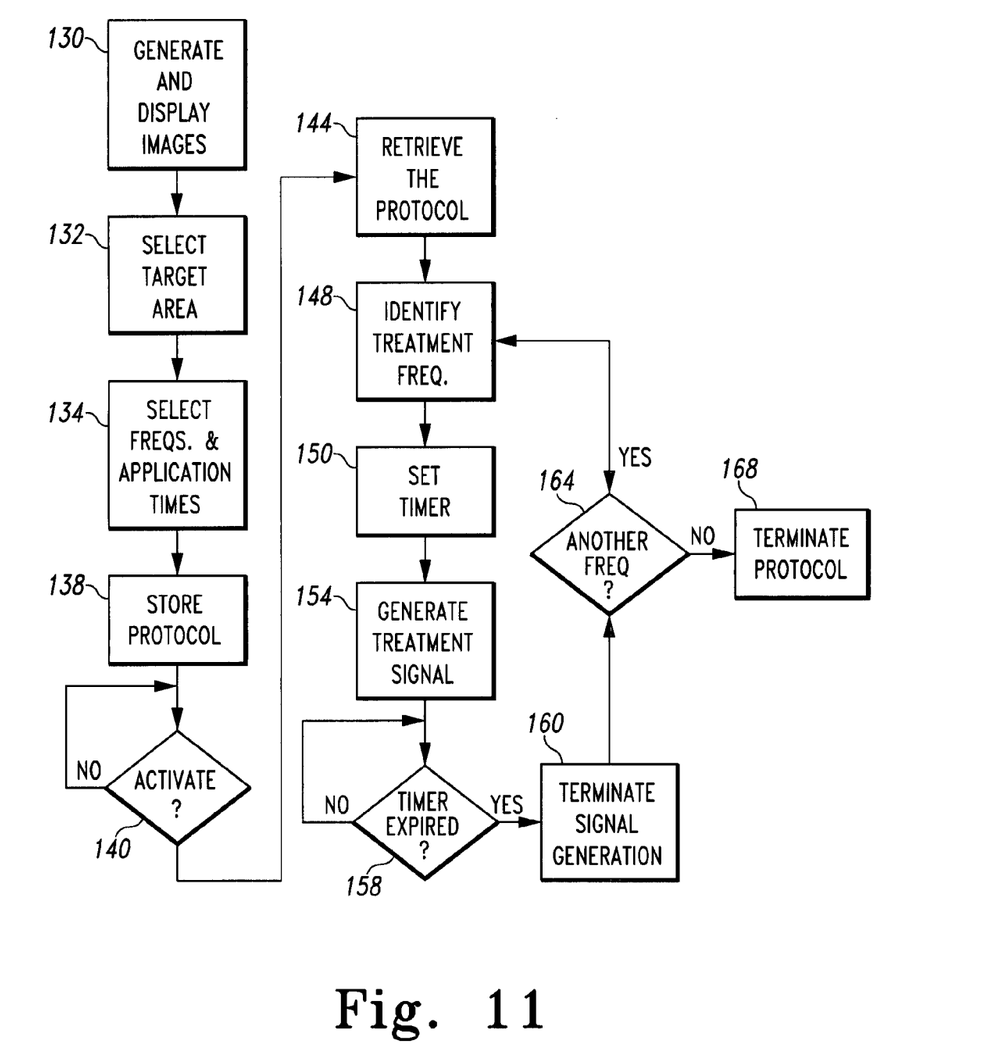
FIG. 11 is a flowchart of an example of a method for treating a patient in accordance with the principles of the present invention.

In an implementation of the present invention, the computer 12 is programmed with instructions for controlling the operation of the treatment system 16. Under the control of the instructions, the computer 12 obtains images of a tissue structure and displays them for a treating physician (block 130). Using the displayed images, a treating physician selects a target area (block 132). If a frequency wave treatment is to be performed, the program enables a user to define one or more frequencies to be used during frequency wave treatment (block 134). The user also specifies a time for the application of each frequency (block 134), although default time periods may be used for application of ultrasound frequencies. The defined treatment protocol may then be stored in the system (block 138). Once the patient has been prepared for the treatment, the ultrasound probe of treatment 16 may be placed in contact with the patient's skin with a transmission jelly as is well known. The stored treatment protocol may then be activated (block 140) and retrieved for execution (block 144). In response to the stored protocol, the computer 12 communicates with the treatment system 16 to identify a frequency for generation of ultrasound waves (block 148) and to set the timer for application of the signal (block 150). System 16 drives the ultrasound wave generators at the identified frequency to apply the treating waves to the target area (block 154). The transducers of the probe may be arranged in a number of configurations that produce different field shapes at the target area. These field shapes include circular spot, ellipsoid, or rectangular spot field shapes. When the treatment system 16 indicates that it is applying the identified frequency to the probe, computer 12 determines when the application period expires (block 158) and sends a signal to the treatment system 16 to terminate generation of the identified frequency (block 160). Of course, the computer 12 may also provide the application timing parameter to the treatment system 16 so that the system 16 determines when to terminate application of the ultrasound waves. Computer 12 determines whether another ultrasound signal is to be applied (block 164) and the process continues until all the identified frequencies have been applied to the target area (blocks 148-160). Execution of the protocol is then terminated (block 168).

The imaging system 14 may be used to evaluate the results of the treatment protocol. Specifically, the imaging system may be an ultrasound system, such as the HDI 5000 system noted above, that is used to image the target area after the treatment protocol has been performed. Parameters such as the density of the target area, the speed of the ultrasound waves in the target area, the attenuation of the ultrasound signals by the target area, and the linearity of the target area's response to the ultrasound signals may be used to determine the results of the treatment protocol. The user selects one or more parameters and the computer 12 sends messages to imaging system 14 to measure the selected parameters. The measurements are returned to the computer 12 for display or the measurements may be displayed at the imaging system 14. If the measurements indicate that the target area tissue has responded satisfactorily to the protocol, the treatment is concluded. Otherwise, the physician may define a new protocol for a second treatment or the physician may decide to apply the stored protocol a second time. Other options may also include the performance of conventional treatment protocols.

Figure 12:
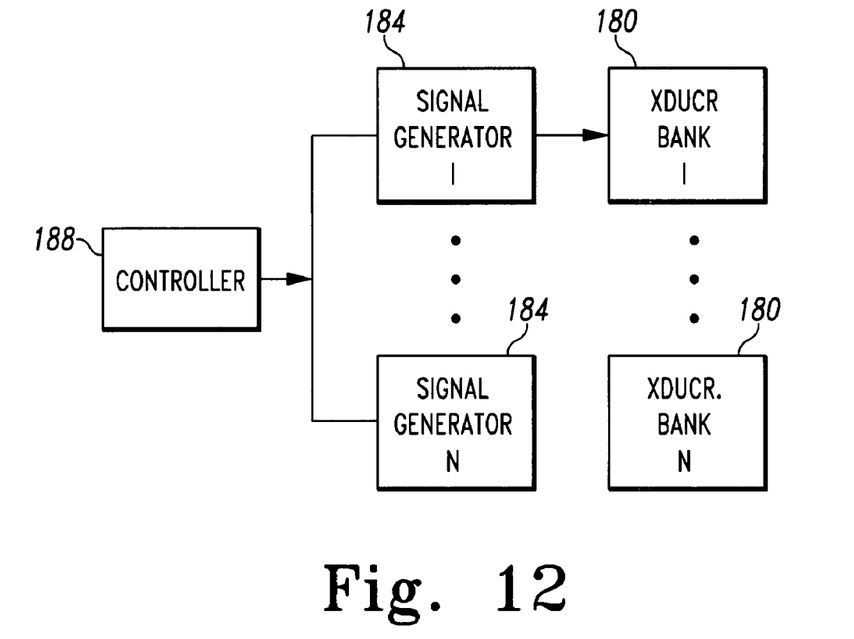
FIG. 12 is a block diagram for a system that may be used to treat a patient's hand with multiple sound frequencies.

A modification to the treatment system 16 that uses a stored protocol is the definition of the treatment protocol. As shown in FIG. 12, the treatment system 16 may include multiple transducer array banks 180, each of which may be coupled to an ultrasound signal generator 184 and a controller 188. The controller 188 receives treatment parameter data from the computer 12 for controlling the operation of the treatment system 16. The computer 12 may be programmed to enable a user to define multiple ultrasound frequencies for application to the target area at the same time. In response to the receipt of multiple frequencies for the generation of ultrasound waves during the same application period, the controller 188 provides each ultrasound generator 184 with a frequency value. Each ultrasound generator 184 then drives the transducer or transducers coupled to the generator at that frequency. The controller 188 may then determine when the application period expires for a particular frequency and deactivate the corresponding ultrasound generator 184. Alternatively, the controller 188 may deactivate an ultrasound generator 184 in response to a signal received from the computer 12 for termination of a particular ultrasound frequency. This implementation of the present invention enables a treating physician to identify multiple ultrasound frequencies for simultaneous or overlapping application to the target area.

Another implementation of a system incorporating the principles of the present invention enables a user to define a change or absolute value for a particular parameter associated with the target area for evaluation of a treatment protocol as it is occurring. In this system, a user selects a parameter associated with the target area, such as acoustic speed, density, linearity, or filtering. The user may then define a change parameter, such as a percentage change, statistical level, or the like. The imaging system 14 then images the target area by generating ultrasonic waves and measuring the selected parameter or parameters to form a baseline for the parameters or parameters. For example, the speed of a wave of one or more particular frequencies through the target area may be measured and stored. Filtering may be measured by determining the power of the reflected signal to determine the amount of signal attenuation occurring through the target area. Then, as the protocol is executed, the parameter is measured and the change in the parameter with respect to the baseline is computed. When the measured change is approximately the same as the user defined change parameter, the computer 12 sends a signal to the treating system 16 to terminate the application of the ultrasound waves. The treating physician may then review the images generated by the imaging system 14 for further evaluation of the protocol's effectiveness. If absolute values are defined by the user, the selected parameter or parameters are measured during the treatment and the computer 12 sends a signal to terminate the treatment in response to the measured parameter being approximately the same as the user defined absolute value.

Figure 13:
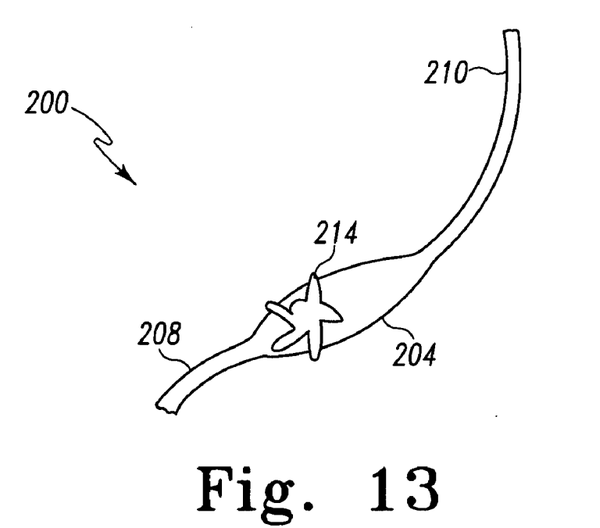
FIG. 13 is an illustration of a surgical probe that may be used to apply a treating sound frequency to a selected target area in accordance with the principles of the present invention.

The system of the present invention may be used in a variety of ways to enhance existing treatment protocols. For example, drug treatment may be enhanced by having a patient ingest a medication, such as an analgesic or anti-inflammatory drug, and then wait for an appropriate period for the drug to available in the patient's bloodstream at the target area. A treatment protocol of ultrasonic radiation may occur to heat the target area and enhance the effect of the medication on the target area. Alternatively, one or more anti-inflammatory medications may be injected into or proximate the target area so that the drug is available for uptake into the target area. A treatment protocol of ultrasonic radiation may be performed to heat the target area and enhance the effect of the medication on the target area. Application of drug therapy in conjunction an ultrasonic therapy protocol may also be applied during an endoscopic procedure. Such a combination may be effective for preparing the target area tissue for surgical treatment. Alternatively, endoscopic techniques may be used to make the target area available for bringing an ultrasonic probe into closer proximity to the target area so that the ultrasonic waves may be more directly focused on the target area. An example of a surgical ultrasonic probe 200 is shown in FIG. 13. As shown in the figure, the body 204 is coupled to an energy source through a cable 208. The head 210 of the probe houses only one or a few transducers and an adjustment knob 214 may be used to adjust the therapy waves applied by probe 200. This arrangement is still effective because the signals from the probe are not attenuated by the subcutaneous layers that are interposed between the probes of FIG. 10 and the target area when the probe is applied to the epidermis of the patient.

While the systems and methods of the present invention have been discussed as using ultrasonic radiation for treatment protocols, other frequencies could be used as well. For example, the imaging system 14 has been described as using ultrasonic and CT imaging techniques, but MRI, and other known imaging techniques may be used, either alone or in conjunction with the described imaging techniques, to identify a target area and to evaluate its parameters as explained above.

There are numerous advantages of the subject invention arising from the various features of the subject invention described herein. It will be noted that further alternative embodiments of the subject invention may not include all of the features described yet still benefit from at least some of the advantages of such features. Those of ordinary skill in the art may readily devise their own implementations of the subject invention that incorporate one or more of the features of the subject invention and that fall within the spirit and scope of the subject invention.

What is claimed is:

1. A method for visualization and treatment of a transverse carpal ligament and surrounding structures/features of a patient comprising:
    placing a probe at a first position with respect to a wrist;
    transmitting a first frequency signal to a carpal tunnel area of the wrist using the probe positioned at the first position;
    generating an ultrasonic image of the carpal tunnel area of the wrist with the first frequency signal;
    identifying a target area of the carpal tunnel area using the generated ultrasonic image;
    moving the probe from the first position to a second position with respect to the wrist, the second position at a location different from the first position; and
    transmitting a second frequency signal to the target area using the probe positioned at the second position, wherein the second frequency signal is at a frequency different from the first frequency signal and is selected to cause at least one of ablation, elongation, necrosis and dissection within the target area.

2. The method of claim 1 wherein the target area identification includes imaging the target area with magnetic resonance imaging.

3. The method of claim 1 wherein the second frequency signal is transmitted in the form of an ellipsoid field.

4. The method of claim 1 wherein the second frequency signal is transmitted in the form of a circular spot field.

5. The method of claim 1 wherein the second frequency signal is transmitted in the form of a rectangular spot field.

6. The method of claim 1 wherein the transmittal of the second frequency signal is performed with a second transducer; and
    the transmittal of the first frequency signal is performed with a first transducer.

7. The method of claim 1 further comprising:
    administering drug therapy before transmitting the second frequency signal to the target area.

8. The method of claim 7 wherein the drug therapy administration is ingesting of a medication prior to the transmission of the second frequency signal to the target area.

9. The method of claim 8 wherein the medication ingested is one of an analgesic and an anti-inflammatory drug.

10. The method of claim 8 wherein the drug therapy administration is injection of a drug to the target area before the transmission of the second frequency signal to the target area.

11. The method of claim 1 wherein the transmission steps are performed with epidermal contact between an ultrasound probe and the skin in the vicinity of the transverse carpal ligament.

12. The method of claim 11 wherein the transmission steps are performed with one of a linear array, curved array, or a tightly curved area probe.

13. The method of claim 1 further comprising:
    defining multiple frequencies for transmission to the target area;
    specifying a duration for the transmission of each defined frequency; and
    transmitting each defined frequency for the specified transmission duration.

14. The method of claim 1 further comprising:
    selecting at least one parameter to be measured for the target area; and
    measuring the selected parameter following transmission of the second frequency signal to determine the effectiveness of the second frequency signal transmission.

15. The method of claim 14 wherein the at least one parameter is selected from the group comprised of target area density, acoustic speed through the target area, signal attenuation in the target area, and linearity of the target area's response to the frequency signal.

16. The method of claim 14 further comprising:
    measuring an initial condition for the selected at least one parameter for a baseline;
    establishing a change parameter for the selected at least one parameter; and
    determining whether a measured value of the selected parameter during transmission of the second frequency signal to the target area is approximately the value of the established change parameter.

17. The method of claim 1 wherein the target area identification includes imaging the target area with spatial compound ultrasound imaging.

18. The method of claim 1 wherein the target area identification includes imaging the target area with a computed tomography scan.

19. The method of claim 1 wherein the transmission of the second frequency signal to the target area is performed subcutaneously.

* * * * *